(12) United States Patent
Nygaard-Petersen

(10) Patent No.: US 8,152,022 B2
(45) Date of Patent: Apr. 10, 2012

(54) COTTON WOOL PAD DISPENSER

(75) Inventor: Anne-Mette Juhl Nygaard-Petersen, Greve (DK)

(73) Assignee: Eazy-Pac Danmark A/S, Holbaek (DK)

( * ) Notice: Subject to any disclaimer, the term of this patent is extended or adjusted under 35 U.S.C. 154(b) by 401 days.

(21) Appl. No.: 12/307,302

(22) PCT Filed: Jul. 3, 2007

(86) PCT No.: PCT/DK2007/000331
§ 371 (c)(1),
(2), (4) Date: May 20, 2009

(87) PCT Pub. No.: WO2008/003316
PCT Pub. Date: Jan. 10, 2008

(65) Prior Publication Data
US 2009/0302051 A1   Dec. 10, 2009

(30) Foreign Application Priority Data

Jul. 4, 2006  (DK) .................................. 2006 00918

(51) Int. Cl.
*A47K 10/24* (2006.01)
(52) U.S. Cl. .............. 221/45; 221/58; 221/63; 221/303; 221/305
(58) Field of Classification Search .................. 221/303, 221/305, 63, 45, 58, 59
See application file for complete search history.

(56) References Cited

U.S. PATENT DOCUMENTS

| | | | |
|---|---|---|---|
| 1,702,573 A * | 2/1929 | Ringler | 221/303 |
| 1,890,295 A | 12/1932 | Jacobs | |
| 2,115,923 A | 5/1938 | Cooper | |
| 2,365,916 A * | 12/1944 | Clifford et al. | 221/303 |
| 3,246,800 A * | 4/1966 | Stone | 221/305 |
| 3,669,307 A * | 6/1972 | Pfund et al. | 221/63 |
| 4,101,053 A | 7/1978 | Mast, Jr. | |
| 5,301,833 A * | 4/1994 | Aycan | 221/96 |
| 5,501,365 A | 3/1996 | Richiger et al. | |
| 5,632,409 A * | 5/1997 | Raghunanan | 221/45 |
| 5,685,643 A * | 11/1997 | Stary | 383/24 |
| 5,704,714 A | 1/1998 | Stary | |
| 5,899,356 A | 5/1999 | Huisman | |
| 6,109,787 A | 8/2000 | Stary | |
| 6,419,113 B1 * | 7/2002 | Tramontina | 221/45 |
| 6,523,717 B1 | 2/2003 | Willemsen | |
| 6,588,626 B2 | 7/2003 | Sauer et al. | |
| 6,789,697 B2 * | 9/2004 | Neess | 221/305 |
| 6,799,695 B1 * | 10/2004 | Borrero | 221/59 |
| 2005/0276653 A1 | 12/2005 | Thiebaut | |

FOREIGN PATENT DOCUMENTS

| | | |
|---|---|---|
| CA | 1070272 A | 1/1980 |
| DE | 4214649 A1 | 11/1993 |
| DE | 202004000696 U1 | 5/2005 |
| EP | 410937 A1 | 1/1991 |

(Continued)

*Primary Examiner* — Mark A Deuble
(74) *Attorney, Agent, or Firm* — Butler, Snow, O'Mara, Steven & Cannada PLLC

(57) ABSTRACT

A packaging for a stack of articles of absorbing materials such as cotton wool tampons or similar hygiene articles, and where the packaging protects the mentioned articles against soiling and spray from above, as well as the sides, and also preventing contamination from below. The packaging can stand steady on the supporting surface and a the same time easily permit the articles withdrawal, one by one, from the packaging. The packaging is constructed with supporting devices so that the withdrawal aperture faces downwards and is elevated above the supporting surface.

10 Claims, 3 Drawing Sheets

FOREIGN PATENT DOCUMENTS

| | | |
|---|---|---|
| EP | 1000872 A1 | 5/2000 |
| FR | 1552684 A | 1/1969 |
| FR | 2749151 A | 12/1997 |
| JP | 08276938 A | 10/1996 |
| RU | 2123464 C1 | 12/1998 |
| RU | 2009103624 | 2/2009 |
| WO | 0001271 A1 | 1/2000 |

\* cited by examiner

COTTON WOOL PAD DISPENSER

BACKGROUND OF THE INVENTION

The invention relates to a packaging for stacking of absorbing materials such as cotton wool tampons and such hygiene articles. The packaging consists of (1) a first end, (2) a second end and (3) a closure face and (4) a cylindrical (rounded) side wall which embodies a storage for the articles and which also connects the first end and the second end to the final closure face and thus enabling the withdrawal of one article at a time. The aperture on at least one side is smaller than the withdrawn article in the same direction, whilst the second end encounters the resting-points that define a resting surface to support the packaging on its supporting surface. The aperture can be re-closed as of free choice.

A packaging of a stacked cotton wool tampons is known from U.S. Pat. No. 1,890,295 A. This packaging is suitable for transport of cotton wool tampons from the production line to retailers and further to the end users and protects the tampons against dust and spray from an area above after the packaging is opened. In connection with the withdrawal (dispensing) of the tampons this packaging includes an aperture, which faces the support face, which also can be closed by a flap, hinged to the underside of the packaging.

FR 1 552 648 A1 discloses a support of the above-mentioned type for flexible sheet-formed articles such as round-shaped cotton wool tampons, where the dispenser is constructed with an aperture that is smaller than the article. The stack of articles is lead towards the dispensing aperture by the aid of an intermediate platform with the help of a spring-loaded device.

The drawback of these types of packagings is that the aperture for removal of the articles is situated on the end face of the packaging, which also forms the supporting platform. Should these packages be placed on the supporting platform such that the end wall with its aperture faces downwards so as to avoid soiling and spray from above, this will enable the end wall to be subject to soil and moisture that is situated below the supporting platform level and thus enabling these impurities to enter the packaging and damage the contents of the packaging.

U.S. Pat. No. 6,588,626 discloses a packaging comprising a first space containing the absorbing material, and a second space, which is situated below the first space. Thus, the first space is elevated above the supporting surface so as to protect this from puddles of water on the supporting surface. The aperture for dispensing the articles is situated in the compartment wall and the articles are therefore not protected in the same way against soil and spray.

US 2005 276653 A1 discloses a dispensing device with a container for dispensing stacked commercial sample single dose cosmetic applicators through an aperture at its bottom. The cosmetic applicators comprise a flat applicator portion and a grasping element or handle containing the sample and positioned perpendicularly to the flat applicator portion when stacked inside the packaging. The packaging comprises a supporting structure connected to the bottom of the container. The supporting structure is in the form of a large foot comprised of a sheet of material, which has been bent twice to form an inverted U-shape. The grasping element extends out of a bottom aperture such that a cosmetic applicator can be withdrawn by pulling the grasping element.

WO 00/01271 A1 discloses a dispensing device for cotton pads adapted for withdrawing such articles one by one. The device comprises an enclosing wall defining an internal volume containing a number of cotton pads stacked with flat surfaces abutting each other in a longitudinal dimension of said volume. The volume terminates in said longitudinal dimension at a first, closed end and at an opposite, second end, said second end comprising an end wall with an aperture for withdrawing an outermost article, a cross-sectional dimension of said aperture being less than a cross-sectional dimension of said stacked articles such as to allow for withdrawing one of said articles nearest to said aperture through said aperture by means of deformation of said article.

The aim of the invention is to produce a packaging for a stack of absorbing materials, such as cotton wool tampons or similar hygiene articles, where the packaging protects the articles against soil and spray from above and the sides as well as prohibits contamination from below and also from the supporting surface. A further purpose is to enable articles to be withdrawn from the packaging one by one.

Another aim of this invention is to produce a packaging with sufficient ventilation in the vicinity around the outmost article, which is not protected by the end walls, and so to eliminate biological contamination in the form of mould and bacterial cultures.

BRIEF SUMMARY OF THE INVENTION

To achieve the above mentioned objects, the device according to the invention is characterized by the features of claim 1. Advantageous embodiments are defined in dependent claims 2-10.

By means of the supporting means the end wall aperture is elevated above the supporting surface and thereby limits the packaging contact area of the part of the packaging, which contains the articles, and thus avoid that any fluids in the vicinity of the supporting surface enter the packaging, damaging this or the contents.

The end with the aperture covers the packaging resting points on which the package can stand. The resting points can at least be three, a rounded edge or comprise one or more surfaces. The resting points are levelled with each other and define the resting surface. When the packaging stands upon the resting surface it then, at all times, supports the packaging's point of gravity.

The second end of the packaging, in comparison to the end wall, forms a resting surface for the protruding support devices of which the resting points, that lie within an outward going distance to the end walls aperture. When the packaging is standing on the resting surface, the aperture faces downwards and is raised higher than the supporting surface. By this, the articles, and especially the outermost article, are protected against dust, soil and spray from above as well as avoiding contact with the supporting surface and soil and moist that can be on the supporting surface.

In accordance with the invention, the packaging is mainly formed as a container of a stiff or semi stiff material such as cardboard, plastic or metal. The rounded surface of the packaging is formed as a tube, which embodies and holds the stack of articles. It is advantageous that the tube has body dimensions that fit the articles' dimensions and form—but can, however, have any other geometric shape. The material should be suitable for eliminating dust and spray—but, as a result of the special construction, which will reduce the packaging contact with the surface, need not be able to sustain continued contact with water other places than the packaging resting points.

This means that the packaging design can have a greater freedom in choice of materials and construction. In a preferred embodiment this can be produced as single use packaging. The packaging can be filled during production and be finally sealed at the first end by folding, heating, welding or adhesion methods or by fitting an end wall. In specific cases, where reusable packaging is used, the packaging's first end can be closed with a removable flap cover allowing refilling.

Basically, the articles can be removed from the packaging in two directions. A radial direction, which is substantially at a 90-degree angle to the axis of the stack or an axial direction, that is substantially parallel to the axis of the stack. In a preferable embodiment the packaging longitudinal axis, which runs from the first to the second end of the packaging, will extend in a parallel axis so that the articles can be withdrawn one by one in that direction.

According to the invention, and in an advantageous embodiment, the supporting device is formed by an elongation of the packaging's circular wall. In this way, the supporting devices can easily be produced at low cost.

When in use in a moist environment it is advantageous that the supporting devices include ventilation openings that permit airflow so as to avoid formation of mould within the area that is enclosed by the packaging's outer wall, the supporting device and the supporting surface.

In an advantageous embodiment the resting points form a straight line. The packaging rests steadily on this closed line, which forms the resting surface. This will reduce the possibility of water damage to the packaging as contact with the supporting surface.

In another embodiment the supporting devices are formed as a number consisting of at least three legs. By this, the packaging rests only on a few points and thus further reduces the possibility of the supporting surface being damaged by fluids. Furthermore, the packaging will be less sensitive to uneven supporting surfaces, thus making the packaging even steadier.

The articles can be forced towards the aperture simply by the weight of the stack of articles, but will mainly be led to this with the aid of an advancing device. I an advantageous embodiment, the advancing device would be formed by the help of an intermediate base, which lies towards the end of the article stack opposite the aperture and thus presses against the opposite end. The thrust force can be attained by attaching the intermediate base to the packaging by the aid of elastic elements, which can be pre-tensioned at the filling stage so that the intermediate base and the stack of articles are forced or drawn to the aperture and thereby brought into contact towards the aperture in the end wall. In accordance with the invention, alternative embodiments such as "screw" devices as known from for example lipsticks, can be implemented.

BRIEF DESCRIPTION OF THE SEVERAL VIEWS OF THE DRAWINGS

The invention is explained below with reference to the drawings. In the drawings the following is shown.

DETAILED DESCRIPTION OF THE INVENTION

Figure 1:
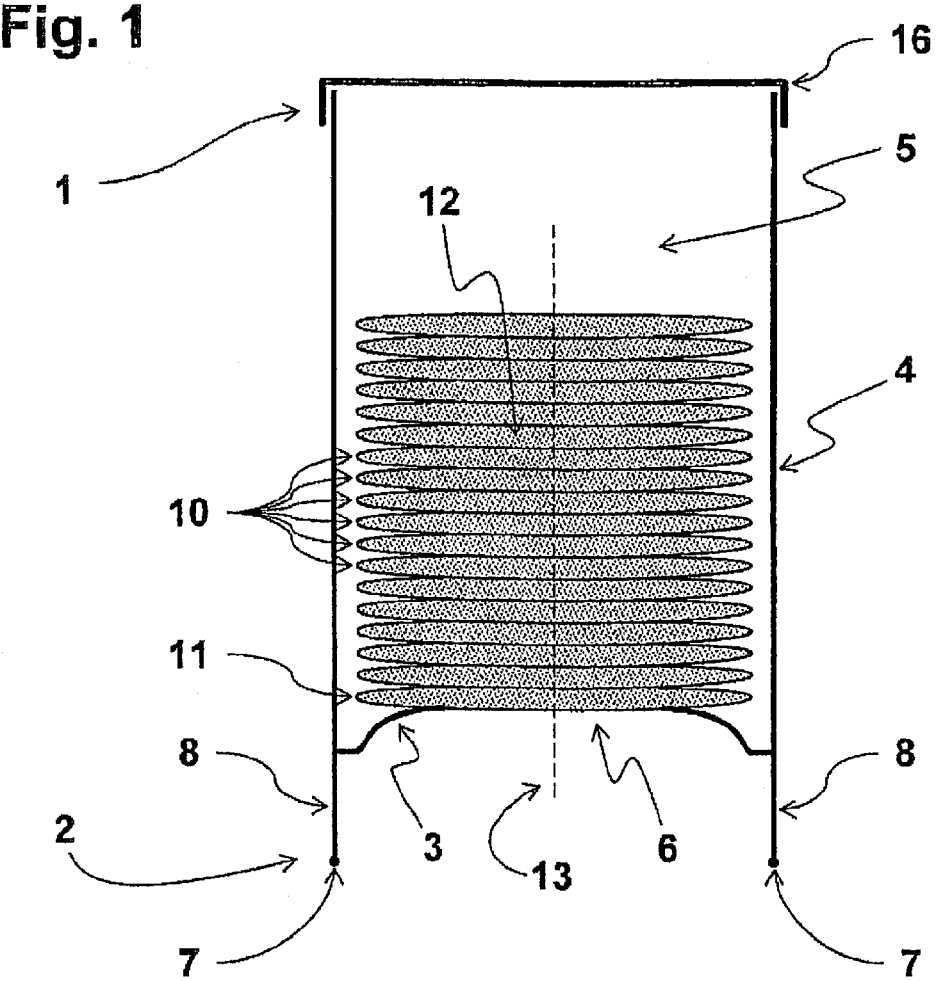
FIG. 1—A first embodiment of a packaging in accordance with the invention.
Figure 2:
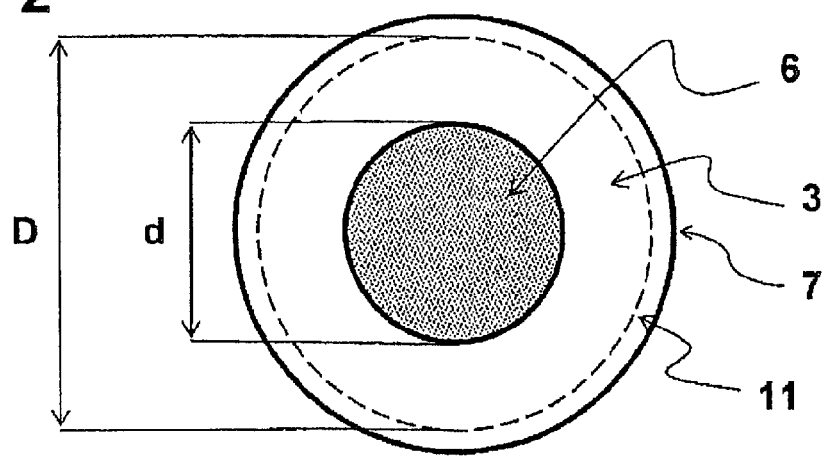
FIG. 2—The packaging in accordance with FIG. 1 and as seen from below.

FIGS. 1 and 2 show a first embodiment of the packaging in accordance with the invention. The packaging comprises a first end, a second end complete with a end-wall, a cylindrical (rounded) wall 4, which encloses a volume area 5 to comprise a stack 12 of flat, flexible and absorbing articles 10. The end-wall 3 covers an aperture 6 for withdrawal of the articles 10. The aperture 6 has a dimension d, in the shown embodiment a diameter of a circular aperture, where the dimension d is less than that of the articles' dimension D in the same direction. The stack of articles 12 lie with the outermost article 11 against the end wall 3 and are retained by this. The outermost article 11 is, however, accessible for withdrawal through aperture 6. The articles 10 can easily be withdrawn one by one by grabbing the outermost article and withdrawing this through aperture 6.

The rounded wall 4 is extended outwards over the aperture 6's level so as to form supporting devices 8. When the packaging is placed on a supporting surface with aperture 6 in the end wall 3 facing downwards, the packaging rests only on supporting points 7 by the supporting devices 8's end. The aperture 6 is elevated above the supporting surface such that articles 10, and especially the outermost article 11, do not come into contact with soil or fluids on the supporting surface. Another advantage with this embodiment is that the packaging's contact with the supporting surface is reduced to a straight supporting face.

The packaging has an advantageous cross section, which is adapted to the articles' dimensions and shape, which in the embodiment of FIGS. 1 and 2 is a round shaped end-wall cross section, which can have another arbitrary geometric shape such as an ellipse or an enclosed polygon. Furthermore, an aperture 6 assumes any shape what-so-ever as long as the conditions are fulfilled so that the aperture 6's dimensions d is less than those of the articles' dimensions D in the same direction.

Figure 3:
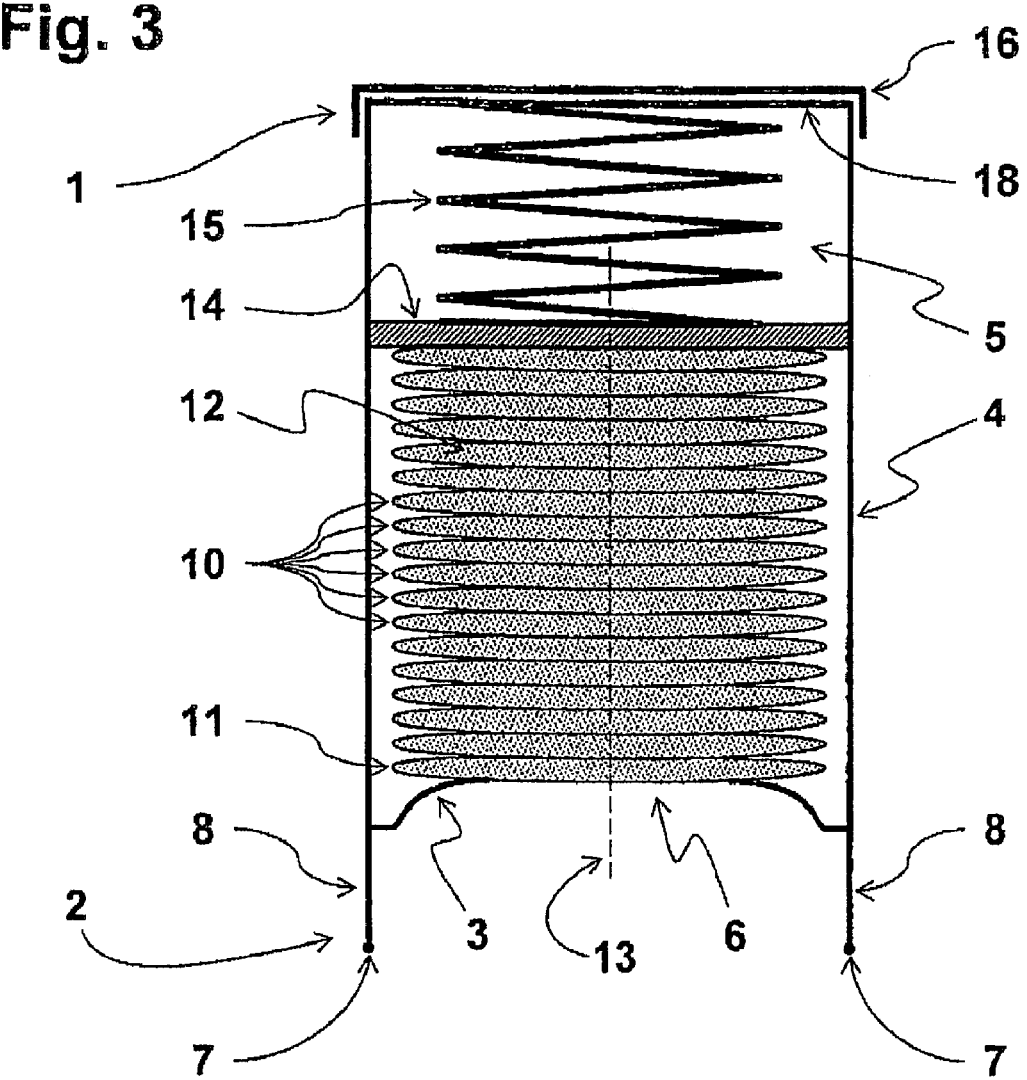
FIG. 3—The packaging in accordance with FIG. 1 showing the spring-loaded intermediate base.

FIG. 3 shows a specifically advantageous embodiment in accordance with the invention where the article stack 12 is in contact towards the aperture 6's end-wall by the aid of an advancing system. In the shown embodiment the advancing system is shaped as an intermediate base 14, which is forced against the article stack's ends that faces away from the aperture by the aid of elastic elements such as springs 15, which connect the intermediate base 14 with the rest of the packaging. In the shown embodiment the spring 15 is a spring-loaded device positioned between the intermediate base 14 and, for this packaging, the associated end-wall 18. The spring 15 is tensioned when filling with articles 10, and the article stack is thus brought into contact with aperture 6. So as to protect the outermost articles 11 during transport the apertures can be held closed with thin foil which can be held in place with an attached lid, which is adjacent to the end-wall 3's side, which faces outwards (is not shown in the drawings). Alternatively, or as a supplement, the packaging can include a lid 16 which, during transport, is fitted on the packaging's second end 2 so as to protect the outermost article 11, and which is demountable and possibly can be fitted on the packaging's first end 1, as shown in FIG. 3.

Figure 4:
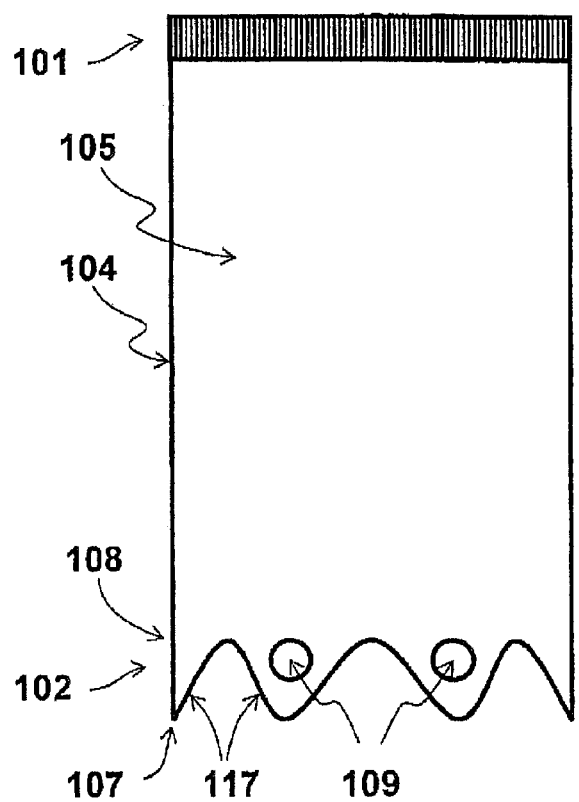
FIG. 4—An alternative embodiment seen from the front of a packaging in accordance with the invention as a tube.
Figure 6:
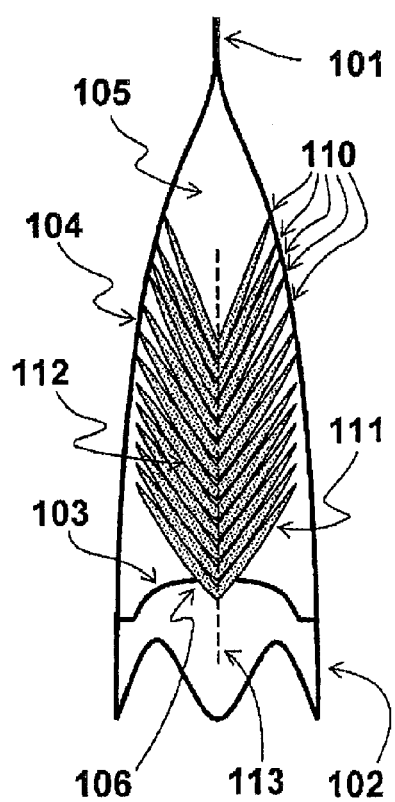
FIG. 6—The packaging in accordance with FIG. 4 seen from below.
Figure 5:
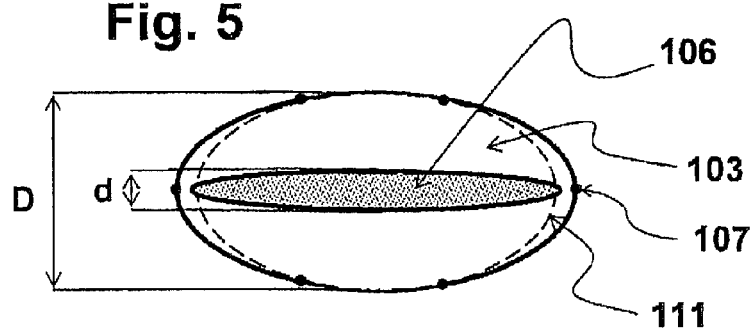
FIG. 5—The packaging in accordance with FIG. 4 seen from the side and in cross section.

FIG. 4-FIG. 6 shows an alternative embodiment for the packaging in accordance to the invention. The packaging is constructed as a tube, where the rounded wall 104 is a tube with a significant elliptical cross section with a small main axis and a larger main axis. The packaging is filled with folded articles 110 as shown in FIG. 5, and the packaging is thereafter closed at its first end 101 by permanently squeezing the rounded wall 104, for example by rabbeting, welding or adhesion. The other end, 102, covers the end-wall 103 with its slit-formed aperture 106. The aperture 106's dimensions d and the folded articles 110's dimensions D in the same direction is measured, as shown in FIG. 5, in parallel with the ellipse's small main axis. The articles 110 press against the aperture 106 on account of the weight and their elasticity, which seeks to elongate each article in a single level. When the outermost article 111 is withdrawn through aperture 106, the following article is drawn towards the aperture as a result of the friction between the articles 110 supported by the above-mentioned elasticity force that seeks to stretch each article to a single level.

When the packaging is placed vertically in the resting points 107, the aperture 106 and thus the whole article stack 112 is elevated above the supporting face by the aid of the supporting device 108, which in the FIG. 4-FIG. 6 shown embodiments is developed as leg 117 forming an extension of the rounded wall 104 towards the end-wall 103. By forming the supporting devices 108 as a leg 117 another advantage is attained as the packaging's contact with the supporting surface is reduced to few resting points 107 without influencing the stability. On the contrary, a packaging standing only on a number of legs 117 and resting on a number of resting points is even more steady on uneven surfaces.

In case of there being fluids on the resting surface, a damp environment can occur within the space internally in the packaging surrounded by the supporting face as well as the supporting devices 108, the end-wall 103 and the outermost article 111. In such damp environments there is a danger of formation of mould and bacterial cultures or other types of biological contamination. So as to avoid accumulation of humid environments in contact with the outermost articles 111 the supporting devices 108 can be developed with ventilation apertures 109 in the form of holes in the side and/or as an intermediate space between the legs 117.

LIST OF REFERENCE NUMBERS 1, 101 The packaging's first end
2, 102 The packaging's second end
3, 103 End-wall
4, 104 Rounded wall
5, 105 The packaging's internal volume
6, 106 Aperture
7, 107 Resting points
8, 108 Supporting devices
10, 110 Articles
11, 111 Outermost article
12, 112 Article stack
13, Article stack axis
14, Intermediate base
15, Spring
16, Cover
18, End-wall at packaging's first end 1, 101
109, Ventilation opening
117, Leg
d, Apertures 61, 106 dimension
D, Articles 10, 110 dimension in the same direction.

The invention claimed is:

1. A dispensing device for flat, flexible, absorbing articles, more specifically cotton wool tampons or cotton pads, adapted for withdrawing such articles one by one,
said device comprising an enclosing wall defining an internal volume containing a number of said articles stacked with flat surfaces abutting each other in a longitudinal dimension of said volume, said longitudinal direction being perpendicular to a cross-sectional dimension,
said volume terminating in said longitudinal dimension at a first, closed end and at an opposite, second end, said second end comprising an end wall with an aperture for withdrawing an outermost article, a cross-sectional dimension of said aperture being less than a cross-sectional dimension of said stacked articles such as to allow for withdrawing one of said articles nearest to said aperture through said aperture by means of deformation of said article,
wherein a supporting structure is positioned near said second end and comprises protruding resting points defining a plane for supporting the device in an upright position on a supporting face such as to position said end wall at a distance from said supporting face, said supporting structure comprising at least one opening or cut-out adapted to allow for withdrawing said outermost article through said aperture and, subsequently, through said opening or cut-out,
said supporting structure having cross-sectional dimensions, which are substantially identical to cross-sectional dimensions of said volume at said second end of said volume, said supporting structure forming a uniform continuation of said enclosing wall, which continuation extends in said longitudinal dimension.

2. A device according to claim 1, wherein said supporting structure is an extension of and is formed integrally with said enclosing wall.

3. A device according to claim 1, wherein said supporting structure is shaped as a wall, which at a distal end is open such as to define an aperture extending in said cross-sectional dimension.

4. A device according to claim 3, wherein a preferably rounded cut-out of said supporting structure wall extends in said longitudinal dimension from said distal end of said supporting structure wall.

5. A device according to claim 1, wherein said supporting structure comprises at least three legs, each of said legs forming one said resting point.

6. A device according to claim 1, wherein said device is cylindrical with a round shape, such as circular or ellipse-shaped, in cross-section.

7. A device according to claim 1, wherein said end wall extends in said cross-sectional dimension.

8. A device according to claim 1, wherein said supporting structure comprises ventilation holes.

9. A device according to claim 1, wherein said resting points form an unbroken line.

10. A device according to claim 1, further comprising means for advancing said stack of articles towards said aperture by means of elastic elements such as springs.

* * * * *